United States Patent [19]

Beck et al.

[11] Patent Number: 4,661,093
[45] Date of Patent: Apr. 28, 1987

[54] METHOD FOR ASPIRATING SECRETED FLUIDS FROM A WOUND

[75] Inventors: Walter Beck, Obere Häslibachstr. 87, CH-8700 Küsnacht; Siegfried Berger, Wernau; Heinz-Peter Werner, Mainz, all of Fed. Rep. of Germany

[73] Assignees: Walter Beck; Margrit Werner, both of Fed. Rep. of Germany

[21] Appl. No.: 618,828

[22] Filed: Jun. 8, 1984

[30] Foreign Application Priority Data

Jun. 11, 1983 [DE] Fed. Rep. of Germany ....... 3321151

[51] Int. Cl.⁴ .............................................. A61M 31/00
[52] U.S. Cl. ........................................ 604/50; 604/52; 604/119; 604/122; 604/123; 604/133; 604/151; 604/152; 604/153
[58] Field of Search ............ 604/51, 52, 133, 151–153, 604/119, 122, 123, 50, 66

[56] References Cited

U.S. PATENT DOCUMENTS

| 1,955,140 | 4/1934 | McKesson | 604/151 |
|---|---|---|---|
| 3,680,562 | 8/1972 | Wittes et al. | 604/51 |
| 3,742,952 | 7/1973 | Magers | 604/133 |
| 3,860,000 | 1/1975 | Wooten et al. | 604/66 |
| 3,961,622 | 6/1976 | Edwards | 604/52 |
| 3,963,027 | 6/1976 | Muriot | 604/151 |
| 4,052,987 | 10/1977 | Wuchinich et al. | 604/65 |
| 4,135,515 | 1/1979 | Muriot | 128/276 |
| 4,186,740 | 2/1980 | Guerra | 604/52 |
| 4,240,433 | 12/1980 | Bordow | 604/51 |
| 4,280,508 | 7/1981 | Barrada | 604/51 |
| 4,291,692 | 9/1981 | Bowman et al. | 604/50 |
| 4,291,694 | 9/1981 | Chai | 604/51 |
| 4,395,258 | 1/1983 | Wang et al. | 604/51 |
| 4,429,693 | 2/1984 | Blake et al. | 604/133 |
| 4,494,950 | 1/1985 | Fischell | 604/66 |
| 4,529,402 | 7/1985 | Weilbacher et al. | 604/133 |

FOREIGN PATENT DOCUMENTS 2371202 6/1978 France .

Primary Examiner—William R. Dixon, Jr.
Assistant Examiner—Margaret B. Medley
Attorney, Agent, or Firm—Wigman & Cohen

[57] ABSTRACT

A method and apparatus for aspirating secreted fluids from a wound is disclosed which involves the placement of a drain into a wound via the tissue adjacent the wound. After the wound is closed, a secretion aspiration and collection device, which is connected to the drain via a tube, is placed into operation. The device is designed to have a suction effect controlled between a minimum value and a maximum value according to the quantity of secreted fluid to be aspirated. This is achieved by one or more sensors which control a tube pump. When a second sensor is used, the pump will not be shut off by a passing air bubble in the fluid. A sleeve may also be provided to facilitate introduction of the drain into the wound. Additionally, a needle may be detachably connected to the sleeve to aid the insertion of the sleeve.

8 Claims, 14 Drawing Figures

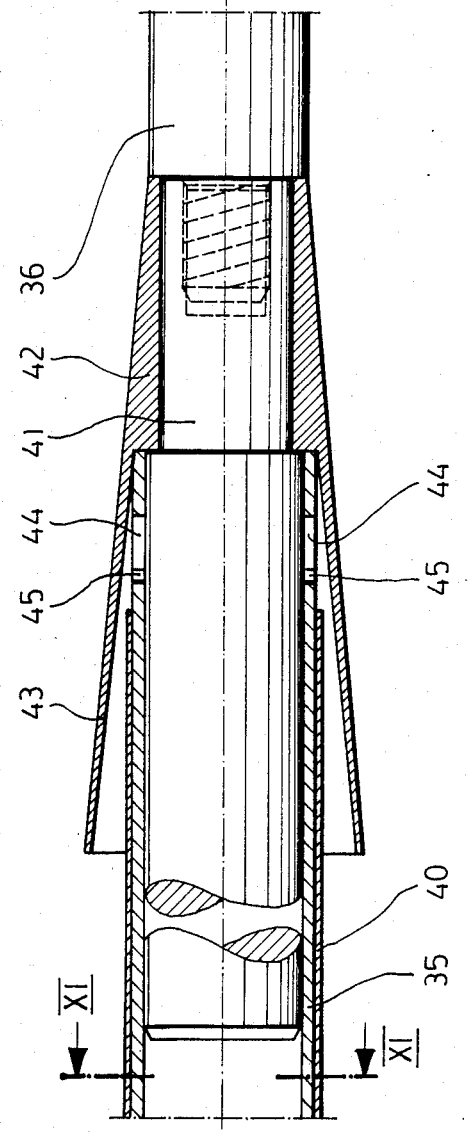

METHOD FOR ASPIRATING SECRETED FLUIDS FROM A WOUND

BACKGROUND OF THE INVENTION

The invention relates to a method for aspirating secreted fluids from a wound, including a method of placement for the drain that accepts the secreted fluid.

Sterile systems are known consisting of a drain, connecting tube, and an evacuated secretion receptacle. Secreted fluids are aspirated from wounds with the aid of this system. Because of the negative pressure in the secretion receptacle, a continuous suction effect is present at the drain, the intensity of which has its maximum at the beginning of the aspiration process and becomes smaller as the container becomes more and more full. In many cases when the secretion aspiration takes place in this manner, the formation of a hemotoma is expected and accepted. It is true that through massage a hematoma reduction can be achieved, but the hematoma formation delays the patient reaching the mobilization phase. Furthermore, with the use of this type of sterile system there is always the danger that, despite the complete sterility of the system, causative organisms can enter the wound. This danger is caused by the fact that the drain must be introduced from the outer surface of the body or from the wound opening, so that any causative organisms located on the surface of the skin can come into contact with the drain in the outer skin layers and thereby get into the wound.

SUMMARY AND OBJECTS OF THE INVENTION

The object of the invention is to create a method for aspirating secreted fluids out of a wound that makes it possible to avoid negative effects on the patient to the maximum extent possible.

The formation of a hematoma or seroma can be avoided by controlling the suction effect between a minimum value and a maximum value according to the quantity of secreted fluid to be aspirated. In addition, by this means it is possible to adapt the suction capacity to the type of wound being treated. The suction capacity can thus be selected to be less than the quantity of occurring secreted fluid when this is desirable for medicinal purposes for the type of wound. This would be the case, for example, for drainages in a bone cavity. This adaption of the suction effect to the quantity of secreted fluid, which takes place even before the beginning of the aspiration process, also prevents damage to the tissue. Additional advantages may be seen from the fact that with this method of aspiration, independence from the position of the tube is assured and a stagnation or even a backflow of the secreted fluid into the wound is prevented, even when the patient moves, thus significantly reducing the likelihood of infection.

If the drain is placed, i.e., introduced into the wound, in the manner defined in claim 2, then causative organisms are reliably prevented from entering the wound because organisms present on the skin surface can only come into contact with the end section of the sleeve, which projects out of the skin surface and is introduced through the tissue from the inside to the outside, and cannot come into contact with the drain, which is introduced into the wound through the sleeve from the outside, but which thereby can only contact the sterile inner wall of the sleeve and not the potentially infected outer side. Since the sleeve is removed outward from the inside out of the tissue, whereby it is drawn away over the tube, organisms on the skin surface can also not get into the tissue or the wound during this phase of the method. Above all, the method according to claim 2 with an embodiment according to claim 3 makes it possible to use a closed suction system, i.e., a unit comprising the drain, the receptacle for secreted fluid and the tube connecting the drain to the receptacle. Such a unit does not need to be opened or become separated either during placement of the drain or during operation.

In a preferred embodiment, after the sleeve is drawn from the tissue, it is cut along its longitudinal direction and removed from the tube so that the sleeve does not need to be continuously arranged on the tube.

Passing the sleeve through the tissue is preferably performed with the aid of a sterile needle detachably connected to the front end of the sleeve. The sleeve and the needle are separated as soon as the front end of the sleeve projects sufficiently far out of the surface of the skin.

The invention has as a further object the creation of an apparatus by means of which the method according to the invention can be performed without difficulty.

The embodiment of the secretion aspiration and collection device according to claim 6 makes possible not only the adaptation of the suction capacity to the quantity of secreted fluid to be aspirated. It also permits the use of a closed, sterile system consisting of the drain, tube, and receptacle, because the tube of this system can be placed into the tube pump without having to be cut. In addition, the tube pump prevents the secreted fluid from standing still or running back. A further advantage is that sacks or bags having a relatively large volume can be used as receptacles, so that an exchange thereof is unnecessary. In contrast, in the known systems an exchange, with an associated opening of the system, is necessary every 16 to 24 hours. There is also the additional advantage that with an embodiment of the receptacle as a plastic bag, the appearance thereof indicates whether the wound is sealed or unsealed The secretion sensor is preferably arranged on the section of the tube lying between the tube pump and the drain. The shorter the distance thereof from the drain, the earlier the secretion sensor can recognize the occurrence of secretion fluid or the end of a secretion of fluid. In one preferred embodiment the secretion sensor is a capacitive or inductive sender, in order for the secretion sensor to be able to operate without direct contact, which is important for hygenic reasons. In such a secretion sensor, the capacitance or inductivity is dependent on whether secretion fluid is located in the tube, which can be made of either plastic or rubber. With a capacitive secretion sensor, for example, the two electrodes surround a portion of the circumference of the tube like a shell.

Since air bubbles can be contained in the secreted fluid and the sensor, when it recognized such air bubbles, would switch the tube pump to its minimum force, which would lead in an undesired manner to a continual switching of the pump between its minimum force and the increased force, a second secretion sensor is arranged on the tube in a preferred embodiment and is displaced relative to the first secretion sensor in the direction of flow, thus preventing a switching of the tube pump to the minimum force by the first secretion sensor when air bubbles carried along in the secretion occur. Preferably this is achieved with the use of identically formed secretion sensors by means of the fact that the signals of the two sensors necessary to release such a switching are joined with each other by a logic circuit. A switching of the pump to its minimum force then only takes place when both secretion sensors find no secretion fluid. If the distance between the secretion sensors is selected to be larger than the length of an air bubble, then an air bubble can no longer lead to a switching of the pump to its minimum force.

The signals produced by the secretion sensor or secretion sensors can be evaluated in various ways for the switching of the tube pump. In one embodiment which is advantageous because of its simplicity and reliability, each present capacitive or inductive secretion sensor lies in the oscillating circuit of an oscillator, the output voltage of which is dependent on the sensor signals with respect to its amplitude. The output voltage of the oscillator or oscillators can then be used after a rectification and amplification to control a power stage which delivers the energy necessary for the operation of the pump.

In a preferred embodiment the interval control has adjusting elements for a variable adjustment of the size of the minimum and maximum suction force of the tube pump. An optimal adaptation of the suction force to the given requirements is then possible. These adjusting elements can be, for example, dials. But a foil keyboard by means of which, for example, various rates of rotation of the tube pump can be given, would also be feasible.

In a preferred embodiment the tube pump is arranged on the outside of a housing containing the interval control. The secretion sensor or secretion sensors can also be located in this housing, whereby free lying connection lines from the sensor or sensors to the interval control, that were necessary when the sensor or sensors were arranged on the tube at a distance from this housing, are eliminated. The arrangement of the sensor or sensors in the housing of the interval control also offers the advantage of being able to better shield the sensors from disruptive influences than if it were located outside the housing. In order to still be able to bring the section of the tube monitored by the sensor or sensors into the immediate vicinity of the sensor or sensors without difficulty, an insert is advantageously provided which can be introduced into the housing of the interval control and is provided with a holder for the tube, so that only the insert, together with the tube, needs to be introduced into the housing in order to allow the sensors to become effective. This insert need not be formed such that the tube must first be attached to it. Rather, the insert can also be part of the one-way system which is discarded after use.

Preferably, a holder is also provided for the attachment of the tube in the tube pump. This holder which together with the tube attached thereto are inserted into a receiving location in the housing of the tube pump, can also be a reusable element or a part of a one-way system.

The penetration of the sleeve through the tissue, by means of which the drain is introduced into the wound, takes place by means of a needle the rear end of which is attached to the sleeve. In order to reliably connect the sleeve with this needle, and yet still make it simple to disconnect the same, a pin which can be inserted into the sleeve is provided in a preferred embodiment on the rear of the needle. This pin can be connected with the sleeve by means of a bayonet connection.

In order to reliably prevent the end of the sleeve projecting beyond the surface of the skin from coming into contact with the skin surface and perhaps causative organisms thereon, a protective sleeve is arranged on the pin of the needle in a preferred embodiment, to which a deformable collar is joined being formed in one piece therewith, which collar overlaps the forward end section of the sleeve and completely covers the outside thereof. This protective sleeve and the collar connected thereto, together with the needle, are separated from the sleeve, so that its end section only becomes exposed after this separation. If the free end section of the collar lies closely against the sleeve or is firmly connected therewith, for example by being glued thereto, which is also possible, and an even better protection against contamination of the forward end of the sleeve results, then prior to the separation of the needle from the sleeve one need only separate the secured end section of the collar from the remaining portion of the collar by a cut with a scalpel.

A needle with a collar of this type can advantageously be employed even in situations when no sleeve is used, but rather where the rear end of the drain, which is separated from the tube, is pressed through the tissue from the side facing the wound. Here too, the collar assures that the end of the drain to be connected with the tube cannot come into contact with causative organisms present on the surface of the skin, i.e., remains sterile.

In order to be able to easily remove the sleeve from the tube despite a simple and economical embodiment after it has been withdrawn from the tissue subsequent to placement of the drain, it is preferably made of plastic and is provided with a slit which extends over its entire length as well as a film hinge lying diametrically opposite said slit. The two halves of the sleeve then only need be opened in order to be able to be removed from the tube. In order not to have to provide any closure elements on the sleeve to hold the sleeve closed while it is introduced into the tissue, it is wrapped over at least a portion of its length in a preferred embodiment by a thin tube of a plastic susceptible to being cut. This tube then only need be cut through with the scalpel in the longitudinal direction in order to open the sleeve and be able to remove it from the tube leading from the drain to the pump.

The invention is described in greater detail below with the aid of exemplary embodiments illustrated in the drawings. Shown are:

BRIEF DESCRIPTION OF THE DRAWINGS

FIG. 10 is an enlarged, partially illustrated longitudinal section through the sleeve and the needle according to the first embodiment;

DETAILED DESCRIPTION OF A PREFERRED EMBODIMENT

Figure 1:
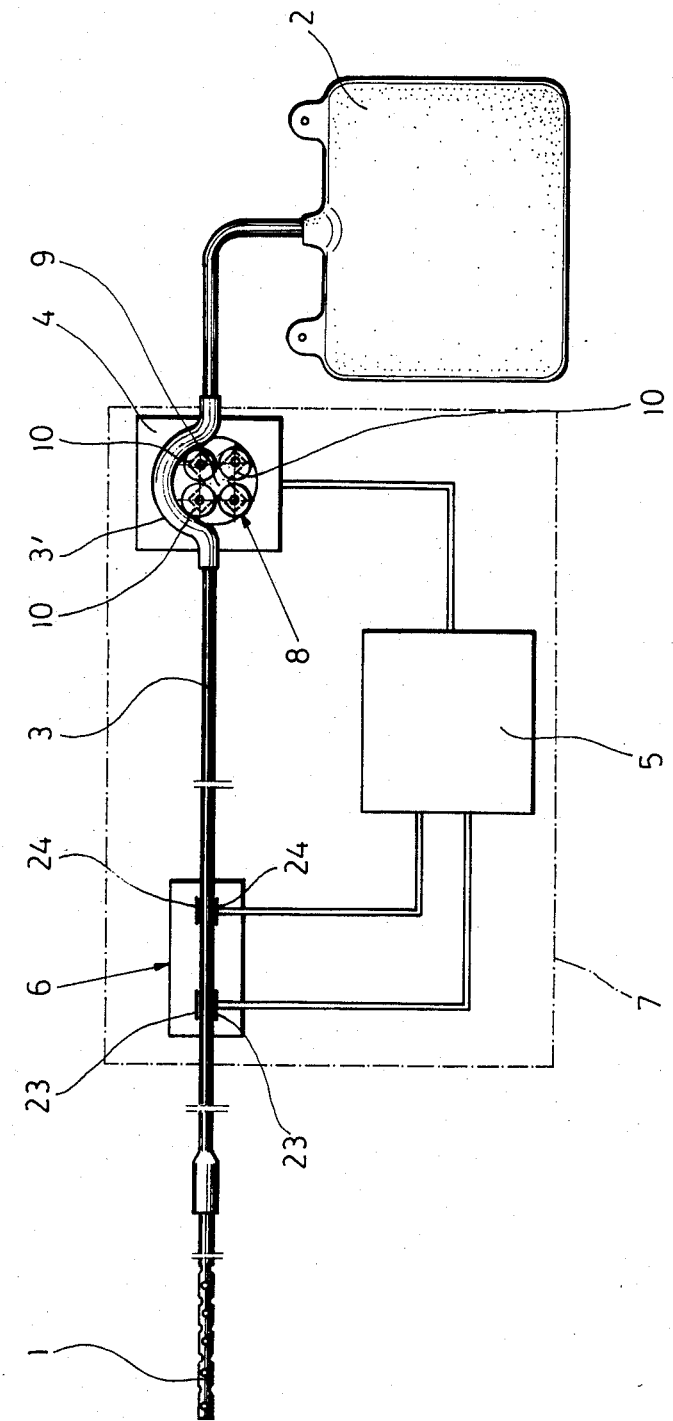
FIG. 1 is a schematic illustration of the aspiration device.

An aspiration device for aspirating secreted fluid out of a wound consists, as shown in FIG. 1, of a drain 1 to be placed in the wound, a tube 3 running from the drain to a receptacle 2, a tube pump 4, a control device 5 which controls the pump, and a sensor device 6. The control device 5 and the sensor device 6 in the exemplary embodiment are located in a housing 7, on which the tube pump 4 is arranged. The receptacle 2 is preferably a plastic bag. The tube 3 in the exemplary embodiment is also made of plastic, with the exception of the section 3' to be attached in the tube pump 4, which is a silicon rubber tube. Because the tube 3 is nondetachably connected with the receptacle 2 and the drain 1, the drain 1, the tube 3 and the receptacle 2 form a closed system, the elements of which that come into contact with the wound and the wound's secreted fluid can be kept sterile and which does not have to be separated for use or during use.

The tube pump 4 includes a pump head 8 arranged on a rotatably mounted drive axis. This pump head 8 comprises, in the exemplary embodiment, a support 9 which is rigidly connected with the drive axis and in the exemplary embodiment is star-shaped, as well as respective rollers 10 arranged on each of the four arms of the support 9. These rollers 10 project over the arm ends and are rotatably mounted on and symmetric to axes lying parallel to the drive axis.

Figure 3:
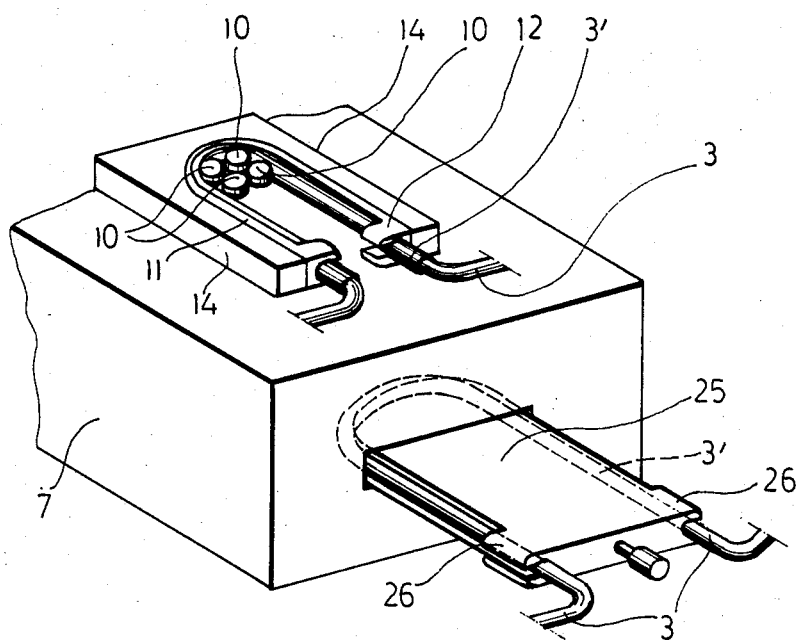
FIG. 3 is a perspective view of the control device and the secretion aspiration pump.

Referring now to FIG. 3, in order to bring the section 3' of the tube 3, on which the rollers 10 must act to achieve the pumping effect, comfortably into the correct position with respect to the pump head 8 and to also hold it in this position, a plastic, channel-like holder 11 is provided, which is provided at both ends with an elastic clamping element 12 that grasps the tube. The holder 11 is either formed as a reusable part of the tube pump or as a part of the throw-away system that always remains connected with the section 3'.

Figure 4:
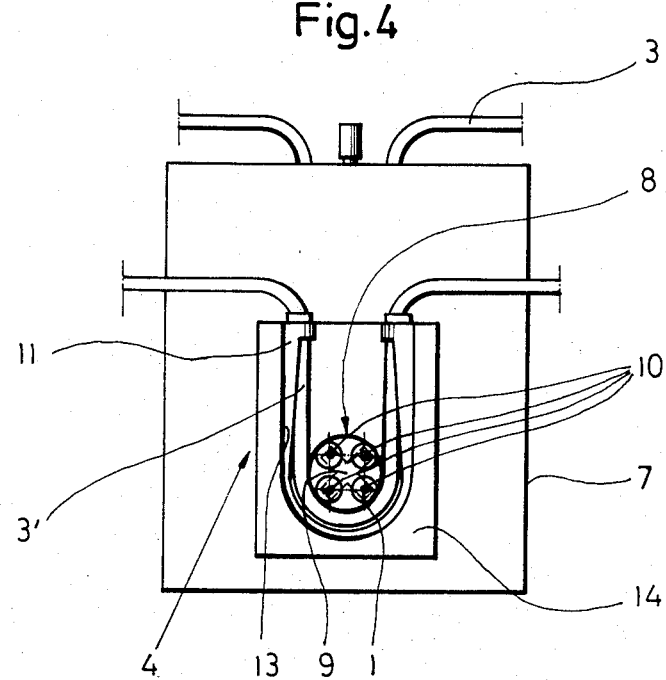
FIG. 4 is a top view of the control device and the secretion aspiration pump.
Figure 5:
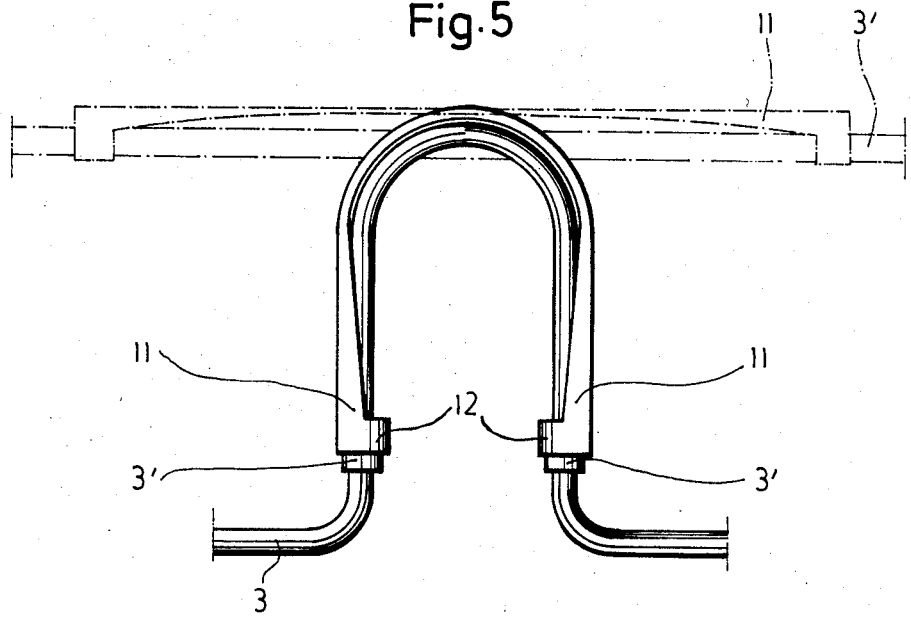
FIG. 5 is a top view of the tube section to be placed into the secretion aspiration pump, together with the holder.

From the extended position illustrated with broken lines in FIG. 5, the holder 11 together with the section 3' of the tube 3 is bent into the U-shaped illustrated with solid lines in FIG. 5 and then placed into a holder 13 (FIG. 4) of a pump housing 14, which supports the pump head 8, whereby the holder 13 supports the U-shaped, bent holder 11 on its dies opposite the tube section 3'. Detent elements (not shown) secure the holder 11 against any shifting in its longitudinal direction.

Figure 6:
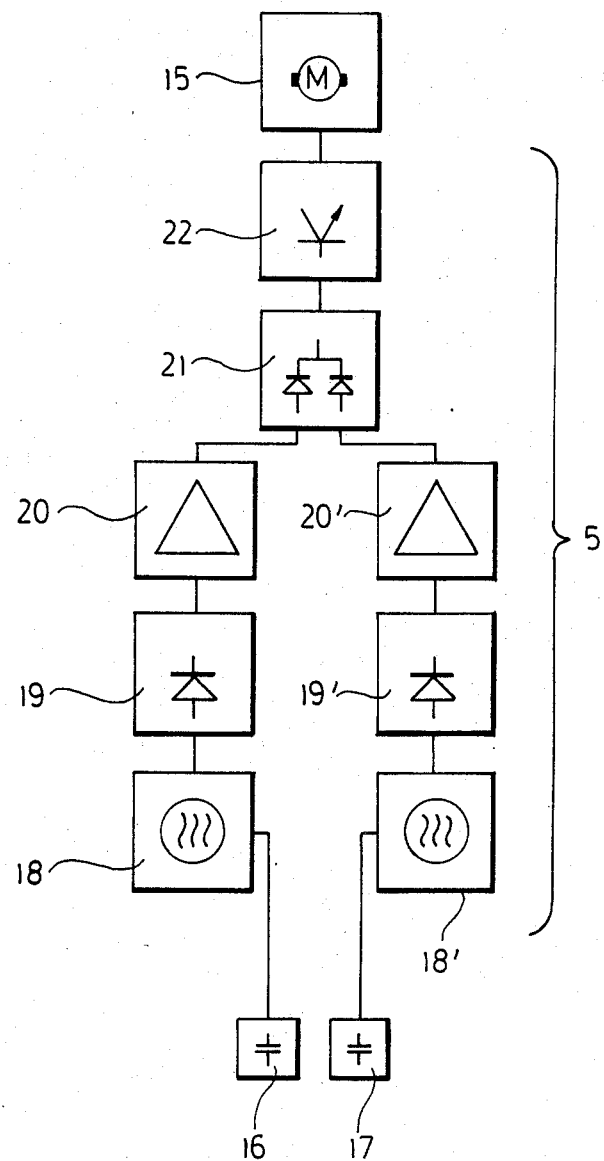
FIG. 6 is the circuit diagram of the aspiration device.

The pump head 8 is driven via a transmission by an electric motor 15, which is formed in a known manner and is therefore shown only schematically (FIG. 6), the rotational speed of which is variable.

The adjustment of the rotational speed of the electric motor 15 takes place by means of the control device 5, which forms an interval control which is connected to two capacitive secretion sensors 16 and 17. The control device 5 has two oscillators 18, 18', behind which are connected voltage rectifiers 19, 19', which rectify the output voltage of the oscillators. The output of these two voltage rectifiers is connected to the input of respective amplifiers 20, 20'. These two amplifiers as well as the two voltage rectifiers and the two oscillators are identical. The output of the amplifier 20 is connected to one input and the output of the other amplifier 20' is connected to the other input of a logic circuit 21, in which an OR switch follows. The output voltage of the logic circuit 21 is led to the input of a power amplifier 22, which lies in the energy supply line of the electric motor 15 of the tube pump 4.

The first capacitive secretion sensor 16 lies in the oscillating circuit of one oscillator 18 and the second capacitive secretion sensor 17 lies in that of the oscillator 18'. Both secretion sensors have two electrodes 23 and 24 (FIG. 1), between which lie two spaced tube sections running in the longitudinal direction of the tube. This distance of the two electrode pairs from each other is greater than the usual length of air bubbles carried along in the secreted fluid.

Because the two electrode pairs 23 and 24 are arranged inside the housing 7, a plastic measurement chamber insert 25 is provided, which, as shown in FIG. 3, has a U-shaped outer form as well as a thickness that is adapted to the diameter of the tube 3. The side surfaces of the measurement chamber insert 25 bordering the outer shape form a channel to receive a section of the tube 3 lying between the drain 1 and the section 3'. Respective shaped clamping elements 26 hold the tube 3 in contact against the measurement chamber insert 25, which can be led through an opening in the rear wall of the housing 7 into the measurement chamber provided in the inside of the housing 7. In the measurement chamber the two electrode pairs 23 and 24 are arranged in such a manner that one or the other of the shanks of the tube 3 that are bent into a U-shape by the abutment against the insert 25, lie between them. Since the measurement chamber insert 25 is an inexpensive plastic element, at the end of the aspiration it can be pulled out of the housing 7 and thrown away together with the tube 3. Of course, it would also be possible to release the tube 3 from the insert 25 and reuse it.

As long as there is no secretion fluid or only a very small quantity of secretion so that between the electrodes 23 and 24 there are only the tube 3 and air and possibly only a small amount of secretion, the two secretion sensors 16 and 17 hold the oscillators 18, 18' in a condition in which their output voltage has a low level. The two output voltages, which are joined with each other in the logic circuit 12, because of their low levels, provide the result that the power amplifier 13 yields such a small voltage that the electric motor 15 connected thereto operates at a selectable rotational speed which corresponds to a desired minimum suction force. A foil keyboard 27 (FIG. 2) is provided on the front plate of the housing 7 to adjust various minimum rotational speeds. However, something such as a dial could also be used in place of such a keyboard. As long as the electric motor 15 operates at its low rotational speed, a control light 28 provided above the foil keyboard 27 is illuminated. In addition, the key of the foil keyboard 27 that was activated to adjust the rotational speed is illuminated.

As soon as one of the two secretion sensors 16 or 17 recognizes a larger amount of secreted fluid, because the secretion rate has increased, the output voltage of one of the two oscillators 18 or 18' reaches a high enough level that the output voltage of the logic circuit 21 effects an output voltage of the power amplifier 22 which leads to an increased rotational speed of the electric motor 15 and thereby to increased force in the tube pump 14. The increased rotational speed of the electric motor 15 can be selected by means of a second foil keyboard 29, which is also provided on the front of the housing 7. And of course this keyboard could also be replaced by other adjusting means, such as a dial. A second control light 30 in the front plate lights up while the electric motor 15 operates with the increased rotational speed. The increased power of the tube pump 4 is selected such that it is sufficient to be able to deliver the maximum rate of occurring secretion into the receptacle 2.

Air bubbles carried with the secretion fluid do indeed result in the first secretion sensor 16 initially, and somewhat later the second secretion sensor 17 effecting a lower level of output voltage of the associated oscillator 18, 18'. But since by the time the second secretion sensor recognizes an air bubble the bubble has already left the effective area of the first secretion sensor, and therefore the level of the output voltage of the oscillator controlled by the first secretion sensor is already back to the higher level, the electric motor 15 continues to operate with the higher rotational speed. A switching of the tube pump to the minimum power is not released by the two secretion sensors 16 and 17 until both detect only air or a reduced quantity of secretion. The tube pump 4 remains in this operating condition until, once again, at least one of the sensors 16 and 17 recognizes a secretion quantity that requires a switching to the higher power level.

Figure 2:
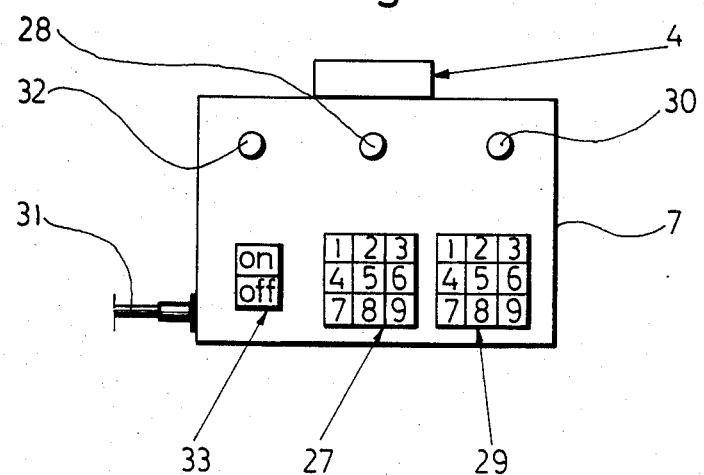
FIG. 2 is a front view of the control device and the secretion aspiration pump.

Normally, the energy for the operation of the electric motor 15 and for the operation of the control device 5 is drawn from the public power supply via a power supply connection line 31 (FIG. 2). In order to prevent the electric motor 15 from stopping during a failure in the power supply, the housing 7 also contains an emergency battery which takes over the energy supply in case of a loss of power. When the emergency battery is in use, a third control light 32 provided in the front plate of the housing 7 is illuminated. In addition, another power switch is provided in the front plate.

Figure 7:
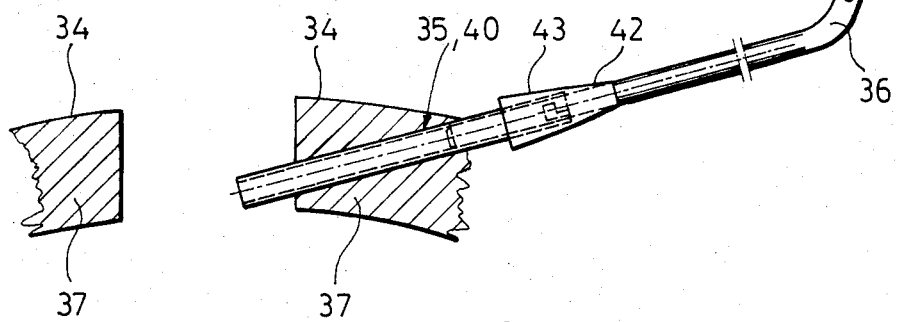
FIG. 7 is a schematic illustration of a first embodiment of a needle with a sleeve coupled thereto after the sleeve has been presssed through the tissue adjacent a wound.
Figure 8:
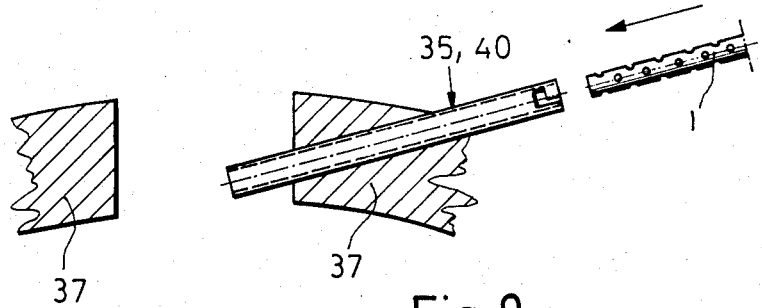
FIG. 8 is a schematic illustration of the sleeve having been pressed through the tissue and of a drain at the beginning of its introduction into the sleeve.

In order to prevent causative organisms found on the skin surface 34 (FIG. 7) from entering the the wound during placement of the drain 1, a sterile, plastic sleeve 35 is used, the inside diameter of which is somewhat larger than the outside diameter of the drain 1. This sleeve 35 is pressed into the tissue 37 adjacent the wound from the inside with the aid of a metal needle 36, and is pressed through this tissue 37 until the sleeve 35 projects somewhat out of the skin surface 34.

Figure 11:
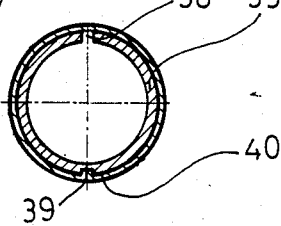
FIG. 11 is a section according to the line XI—XI of FIG. 10.

As shown in FIG. 11, the sleeve 35 is provided with a longitudinal slot 38 which extends over its entire length. Diametrically opposite the longitudinal slot 38 is a recess 39 which also extends over the entire length and forms a film hinge. A thin foil tube 40 made of a plastic foil that is easy to cut is drawn over the sleeve 35 and holds the longitudinal slot 38 closed.

As shown in FIG. 10, a displaced pin 41 is coaxially threaded to the rear end of the needle 36. A plastic conical bushing 42 is pushed onto the smaller diameter portion of this pin adjacent to the end of the needle. The outside diameter of this conical bushing 42 at the end bordering on the needle 36 is equal to the outside diameter of the cylindrical lance and uniformly increases toward the other end until it reaches a value somewhat larger than the outside diameter of the sleeve 35. At this end there is joined thereto, in one piece therewith, a collar 43, the wall thickness of which is selected to be small enough that the collar 43 can easily be deformed. As shown in FIG. 10, the collar 43 has a conical shape so that it forms an extension of the conical bushing 42 which overlaps a portion of the end of the sleeve 35 adjacent the conical bushing 42 as well as the associated end section of the foil tube 40. The larger diameter section of the pin 41 has an outside diameter adapted to the inside diameter of the sleeve 35, so that the sleeve 35 can be pushed over this section of the pin 41 until it abuts the end of the conical bushing 42. Two diametrically opposite radial projections 44 on the portion of the pin 41 containing the sleeve 35, together with respective bent-angle slots 45 on the end section adjacent the conical bushing 42 form a bayonet closure by means of which the sleeve 35 can be form-fittingly connected with the needle 36 via the pins 41 and can be easily separated from the needle by a simple rotation. After the sleeve 35, with the aid of the needle 36, has been pushed from the inside through the tissue 37 to the point that the full length of the collar 43 is exposed, the needle 36 is rotated relative to the sleeve 35 in the direction of release for a bayonet closure and it is then removed from the end of the sleeve together with the pin 41, the conical bushing 42, and the collar 43. Thanks to the collar 43, the end of the sleeve 35 projecting out of the skin surface 34 has not come into contact with the surface of the skin 34 over a sufficiently large length so that when the drain 1 is then introduced into the outwardly extending end of the sleeve 35, the drain safely does not come into contact with the portions of the sleeve 35 that are contaminated, i.e., have come into contact with the surface of the skin 34.

Figure 9:
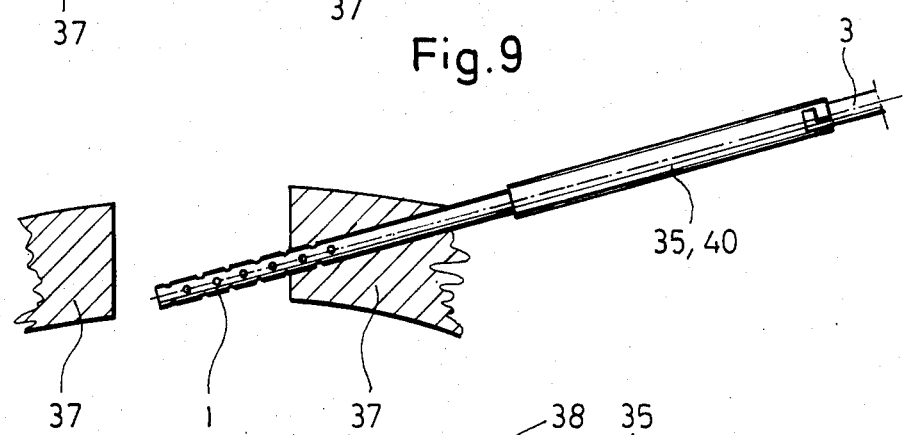
FIG. 9 is a schematic illustration of the position of the drain after having passed through the sleeve and after withdrawal of the sleeve from the tissue.

After the drain 1 has been placed in the wound, the sleeve 35 is drawn out of the tissue 37 over the drain or the tube 3, as shown in FIG. 9. One need then only cut through the foil tube 40 in the longitudinal direction with the scalpel in order to be able to open the sleeve 35 and remove it from the tube 3. After closure of the wound the tube pump is first placed into operation at the low suction rate. It then automatically increases the suction force when necessary due to the secretion sensors 16 and 17.

Figure 12:
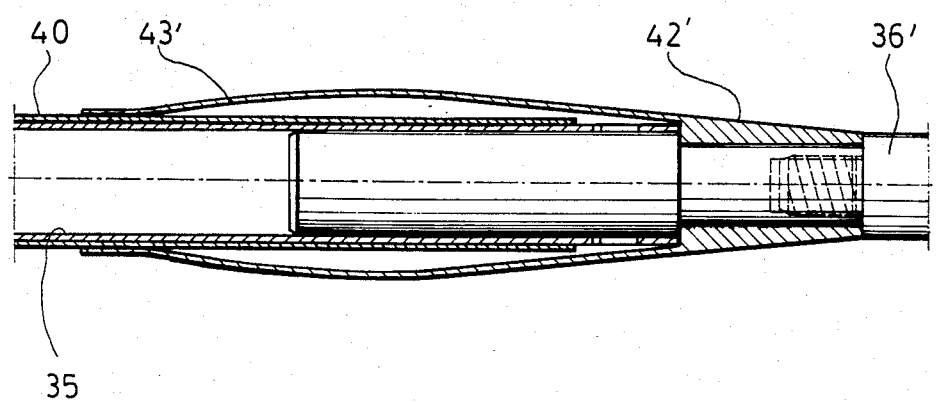
FIG. 12 is a partially illustrated longitudinal section of a needle according to a second embodiment in connection with a sleeve.

A modified embodiment of a needle is illustrated in FIG. 12 which is distinguished from the above-described needle illustrated particularly in FIG. 10 only in that in the area of its end section opposite the conical bushing, the collar 43' of the conical bushing 42' placed on the rear needle end lies closely against the outer surface of the foil tube 40 and is glued thereto. This reliably excludes the possibility of causative organisms being able to enter the section of the sleeve 35 and of the foil tube 40 overlapped by the collar 43'. Because of further details concerning the embodiment of the needle 36', the conical bushing 42', and the connection of s the needle 36' with the sleeve 35, reference will be made to FIG. 10 and the associated text to the extent that there are no differences.

Figure 13:
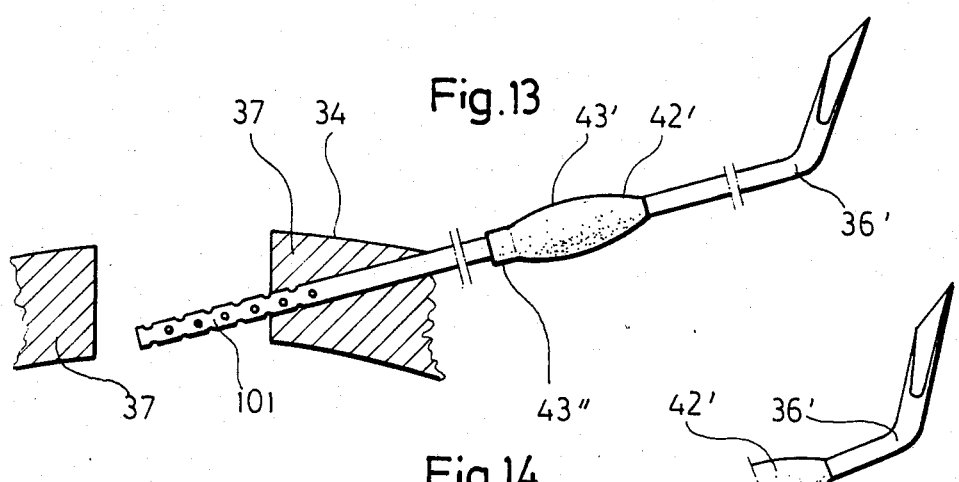
FIG. 13 is a schematic illustration of a drain having passed through tissue by means of a needle according to FIG. 12.
Figure 14:
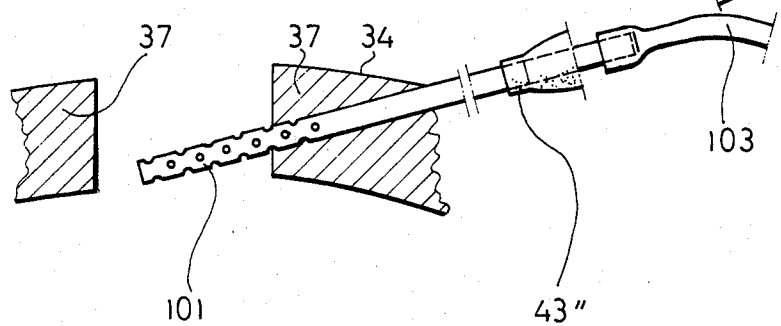
FIG. 14 is a schematic illustration of the drain placed according to FIG. 13 after separation of the needle and the subsequently completed connection with a tube.

As shown in FIGS. 13 and 14, the needle 36' with its conical bushing 42' and the collar 43' formed in one piece therewith can also be used to advantage in the placement of a drain even when the sleeve 35 has not previously been pressed through the tissue 37 adjacent the wound.

This is also true, of course, for the needle 36 with its conical sleeve 42 and the collar 43.

Both the collar 43 and the collar 43' namely enclose the end section of the drain 101 to be connected with the needle 36 and thereby prevent this end section from coming into contact with causative organisms on the surface of the skin 34 as the skin is penetrated. If a needle 36' with a collar 43' is used, the free end section of which is secured to the end of the drain, then the end section 43" securely connected with the drain 101 is separated from the remaining portion of the collar 43' by a cut with a scalpel before the needle 36' is separated from the drain 101. The separation of the needle from the drain is easily performed with the use of a needle 36 with a collar 43. The end section of the drain 0 101 no longer covered by the collar 43 or 43' is free of germs. Therefore, no germs can enter the system from this area if the drain 101 is then coupled with a tube 103, as illustrated in FIG. 14.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for aspirating secreted fluid out of a wound comprising the steps of:
    (a) connecting a drain via a tube with a secretion aspiration and collection device to form a sterile system;
    (b) placing said drain into the wound through tissue adjacent the wound;
    (c) closing said wound;
    (d) placing said secretion aspiration and collection device into operation, said secretion aspiration and collection device having a suction effect controlled between a minimum value and a maximum value;
    (e) sensing the amount of fluid secreted by the wound; and
    (f) varying said suction effect by means of a tube pump on the basis of the quantity of secreted fluid sensed in the wound to be aspirated.

2. The method according to claim 1 further comprising the steps of:
    (a) introducing a sterile sleeve into the tissue adjacent the wound from the wound side of the tissue;
    (b) pushing said sterile sleeve outward through the tissue toward a body surface defining an outward surface of the tissue in such a manner that a forward end of said sleeve projects above said body surface and a rear end of said sleeve still lies in the wound;
    (c) introducing said drain into the wound through said sleeve; and
    (d) withdrawing said sleeve outwardly from the tissue.

3. The method according to claim 2 wherein said drain is introduced into the wound through said sleeve from the forward end of said sleeve.

4. The method according to claim 3 further comprising the steps of:
    (a) parting said sleeve longitudinally after withdrawing said sleeve from the tissue; and
    (b) removing said sleeve from said tube connecting said drain with said secretion aspiration and collection device.

5. The method according to claim 4 further comprising the steps of:
    (a) using a sterile needle detachably connected to the forward end of said sleeve to facilitate said step of introducing said sleeve into said tissue; and
    (b) detaching said sleeve from said needle.

6. The method of claim 1 further including the steps of providing sensing means for measuring the quantity of fluid in the wound.

7. The method of claim 6 wherein said sensing means is a capacitive or inductive sender.

8. The method of claim 6 wherein said sensing means is positioned on the section of tube between a tube pump and said drain.

* * * * *

UNITED STATES PATENT AND TRADEMARK OFFICE
CERTIFICATE OF CORRECTION

PATENT NO. : 4,661,093
DATED : April 28, 1987
INVENTOR(S) : WALTER BECK et al

It is certified that error appears in the above-identified patent and that said Letters Patent is hereby corrected as shown below:

IN THE SPECIFICATION:

Column 8, line 68, after "of" delete "s";

Column 9, line 24, after "drain" delete "0".

IN THE CLAIMS:

Column 9, line 40, after "sterile" insert --and closed--.

Signed and Sealed this

Eighth Day of September, 1987

Attest:

DONALD J. QUIGG

Attesting Officer

Commissioner of Patents and Trademarks